US005359996A

United States Patent [19]

Hood

[11] Patent Number: 5,359,996

[45] Date of Patent: Nov. 1, 1994

[54] ULTRASONIC CUTTING TIP AND ASSEMBLY

[75] Inventor: Larry L. Hood, Laguna Hills, Calif.

[73] Assignee: Nestle, S.A., Switzerland

[21] Appl. No.: 588,396

[22] Filed: Sep. 26, 1990

Related U.S. Application Data

[62] Division of Ser. No. 260,702, Oct. 21, 1988, Pat. No. 4,989,583.

[51] Int. Cl.$^5$ .............................................. A61B 17/20

[52] U.S. Cl. ......................................... 604/22; 606/28

[58] Field of Search ........................ 128/24 A; 604/22

[56] References Cited

U.S. PATENT DOCUMENTS

| | | | |
|---|---|---|---|
| 3,133,351 | 5/1964 | Von Seggern | 433/86 |
| 3,584,327 | 4/1969 | Murry | 128/24 A |
| 3,589,363 | 6/1971 | Banko et al. | 128/24 A |
| 3,693,613 | 9/1972 | Kelman | 128/24 A |
| 3,732,858 | 5/1973 | Banko | 604/22 |
| 3,823,477 | 7/1974 | Hedrick | 128/24 A |
| 3,896,811 | 7/1975 | Storz | 128/24 A |
| 3,942,519 | 3/1976 | Shock | 128/24 A |
| 3,945,375 | 3/1976 | Banko | 128/6 |
| 3,990,452 | 11/1976 | Murry et al. | 128/24 A |
| 4,011,869 | 3/1977 | Seiler, Jr. | 604/22 |
| 4,063,557 | 12/1977 | Wuchinich et al. | 128/24 A |
| 4,330,278 | 5/1982 | Martin | 433/81 |
| 4,417,578 | 11/1983 | Banko | 604/22 |
| 4,425,115 | 1/1984 | Wuchinich | 604/22 |
| 4,428,748 | 1/1984 | Peyman et al. | 604/22 |
| 4,515,583 | 5/1985 | Sorich | 604/22 |
| 4,516,398 | 5/1985 | Wuchinich | 604/22 |
| 4,517,977 | 5/1985 | Frost | 604/22 |
| 4,526,571 | 7/1985 | Wuchinich | 604/22 |
| 4,531,934 | 6/1985 | Kossovsky et al. | 604/22 |
| 4,535,759 | 8/1985 | Polk et al. | 128/24 A |
| 4,589,415 | 5/1986 | Haaga | 128/328 |
| 4,609,368 | 9/1986 | Dotson, Jr. | 604/22 |
| 4,660,573 | 4/1987 | Brumbach | 128/328 |
| 4,681,561 | 7/1987 | Hood et al. | 604/22 |
| 4,721,107 | 1/1988 | Bolg et al. | 128/24 A |
| 4,729,373 | 3/1988 | Payman | 604/22 |
| 4,741,731 | 5/1988 | Starck et al. | 604/22 |
| 4,748,971 | 6/1988 | Borodulin et al. | 128/24 A |
| 4,787,889 | 11/1988 | Steppe et al. | 604/22 |
| 4,816,018 | 3/1989 | Parisi | 128/24 A |
| 4,832,021 | 5/1989 | Kuhl et al. | 269/787 |
| 4,867,141 | 9/1989 | Nakada et al. | 128/24 A |
| 4,869,715 | 9/1989 | Sherburne | 604/22 |
| 4,886,060 | 12/1989 | Wiksell | 128/24 A |
| 4,921,476 | 5/1990 | Wuchinich | 604/22 |

FOREIGN PATENT DOCUMENTS

| | | |
|---|---|---|
| 2363192 | 7/1974 | Germany . |
| 3532405 | 3/1987 | Germany . |
| WO86/07249 | 12/1986 | WIPO . |
| WO87/05793 | 10/1987 | WIPO . |

*Primary Examiner*—Francis Jaworski
*Attorney, Agent, or Firm*—James Arno; Jeffrey S. Schira; Christopher W. Brody

[57] ABSTRACT

An ultrasonic cutting tip assembly for an ultrasonic surgical cutting instrument having an ultrasonic transducer. The assembly includes a transition horn which is operatively couplable to the transducer, an elongated ultrasonic vibration-transmitting tube which is separable from the horn, and a threaded retaining nut. The threaded portion of the nut threadably engages the threaded portion of the transition horn to hold the proximal end of the tube and the horn together so that ultrasonic vibrations can thereby be efficiently transmitted from the transducer to the distal end of the tube, and then to the surgical site. The nut threaded portion can be formed either on the outside or the inside of the nut, and when on the outside in one embodiment, the nut and tube can be formed as an integral member to be threaded into the distal end of the horn. The elimination of all exposed tip nut surface angles greater than forty-five degrees increases the hydrodynamic performance of the assembly.

34 Claims, 5 Drawing Sheets

ULTRASONIC CUTTING TIP AND ASSEMBLY

This application is a division of application Ser. No. 07/260,702 filed Oct. 21, 1988 now U.S. Pat. No. 4,989,583.

BACKGROUND OF THE INVENTION

This invention relates to ultrasonic surgical cutting instruments and more particularly to the cutting tip assemblies thereof. It also pertains to ultrasonic cutting tip assemblies whose tools or tubes are removable or separable from their ultrasonic transition horns.

Devices which effectively utilize ultrasonic energy for variety of applications are well known in a number of diverse arts. The application of ultrasonically vibrating surgical devices used to fragment and remove unwanted tissue with significant precision and safety has thus led to the development of a number of valuable surgical procedures. Accordingly, the use of ultrasonic aspirators for the fragmentation and surgical removal of tissue from a body has become well known. Initially, the technique of surgical aspiration was applied for the fragmentation and removal of cataract tissue as shown, for example, in U.S. Pat. Nos. 3,589,363 and 3,693,613. (Each of the patents and other documents mentioned herein is hereby incorporated by reference in its entirety.) Later, such techniques were applied with significant success to neurosurgery and other surgical specialties where the application of ultrasonic technology through a small, handheld device for selectively removing tissue on a layer-by-layer basis with precise control has proven feasible.

Certain devices known in the art characteristically produce continuous vibrations having a substantial constant amplitude at a frequency of about twenty to thirty kHz up to about forty to fifty kHz. U.S. Pat. No. 3,589,363 describes one such device which is especially adapted for use in the removal of cataracts, while U.S. Pat. No. 4,063,557 describes a device suitable for the removal of soft tissue which is particularly adapted for removing highly compliant elastic tissue mixed with blood. Such devices are continuously operative when a surgeon wishes to fragment and remove tissue, and generally operate under the control of a footswitch easily accessible to him.

Another ultrasonic surgical instrument is disclosed in U.S. Pat. No. 3,990,452 to Murry et al. Solid or two piece brazed tips for a conical or exponential type of sectional concentrator are illustrated therein. The flats that are subsequently machined on both sides of the tip nut for wrench tightening are right angle notches, which add additional loading to the handpiece and cause additional cavitation bubbles to form. Further, not only does the brazing thereof add an costly step to the manufacturing process, but the copper and silver content can be harmful to the patient's living tissue. Additionally, the large rigid nut of this instrument makes a good, consistent, low impedance acoustical coupling more difficult.

Certain limitations have emerged, and in particular, the promise of safe, effective emulsification and removal of unhealthy tissue and especially hard tissue, such as cataract, while minimizing damage to adjacent healthy tissue, has not yet been fully and truly realized. Many of the prior art ultrasonic surgical cutting or emulsifying instruments ineffectively utilize the power supplied to vibrate them and also have proven to be expensive to manufacture. Further, designs of some instruments do not allow the surgeon to easily visualize the surgical procedure at the surgical site and to manipulate the vibrating tool accurately and consistently during each of the procedures. Thus, a need has arisen for an improved ultrasonic cutting tip assembly design.

OBJECTS OF THE INVENTION

Accordingly, it is a principal object of the present invention to provide an improved ultrasonic cutting tip assembly for an ultrasonic surgical cutting instrument having an ultrasonic transducer.

A further object of the present invention is to provide an ultrasonic cutting tip assembly which is less expensive to manufacture so as a practical matter to be truly disposable.

A still further object of the present invention is to provide an improved cutting tip assembly design which minimizes the cavitation erosion of the tip and thereby also the deposition of metallic particulates at the surgical site, such as in the eye.

Another object is to provide an improved cutting tip assembly design which reduces adjacent tissue heating which can cause in cataract removal procedures corneal burns and astigmatism, without deleteriously affecting the surgical removal procedures.

A further object is to provide an improved cutting tip assembly design which minimizes the production of cavitation bubbles which can visually interfere with the surgical procedure such as in a cataract removal procedure.

A still further object of the present invention is to provide an improved cutting tip assembly design which reduces the power required to produce the same tool tip end vibration.

Another object is to provide an improved cutting tip assembly design which reduces the exposure of adjacent healthy tissue to the ultrasound energy.

A further object is to provide an improved cutting tip assembly construction which provides a better fluidic seal for the cutting tip.

A still further object is to provide an improved cutting tip assembly design which handles greater tensile forces and accelerations.

Another object is to provide a cutting tip assembly having improved acoustic gain variations and stability.

A further object is to provide an improved ultrasonic cutting tip assembly which provides increased resulting emulsifying forces.

A still further object is to provide an improved ultrasonic cutting tip assembly design which allows tissue resection to be performed on harder tissue, such as that of a cataract lens, with less damage to adjacent healthy tissue.

Another object is to provide an ultrasonic cutting tip assembly having good, consistent, low impedence acoustical coupling characteristics.

A further object is to provide a cutting tip assembly wherein low cost metal forming technology is utilized in the manufacture thereof and which is efficient in providing a higher stroke for less input power.

Other objects and advantages of the present invention will be more apparent to those skilled in the art from the following description taken in conjunction with the accompanying drawings.

DETAILED DESCRIPTION OF THE PREFERRED EMBODIMENTS

Figure 1:
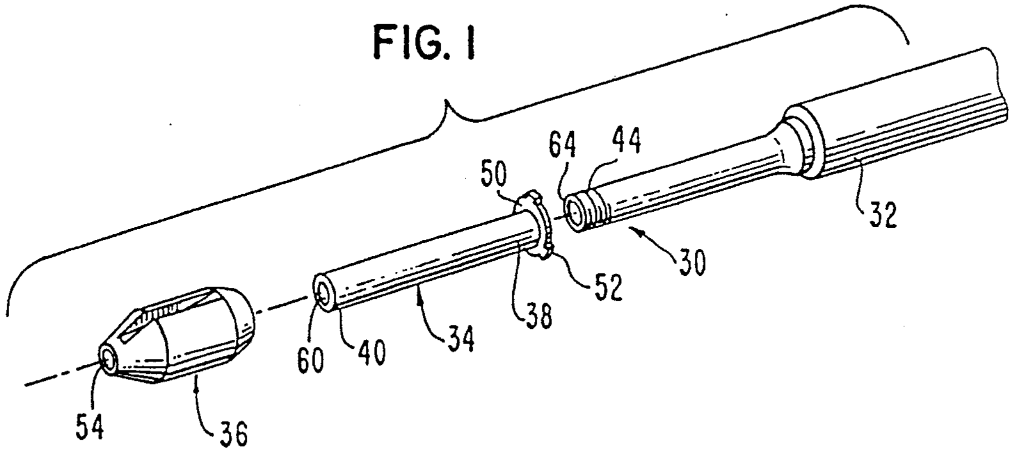
FIG. 1 is an exploded perspective view of a first embodiment of the present invention.

Referring to FIGS. 1–4, an ultrasonic cutting tip assembly adaptable to generally any ultrasonic surgical cutting instrument or handpiece is illustrated generally at 30. The assembly 30 includes a transition horn 32 which is operatively couplable to an ultrasonic transducer of the ultrasonic surgical cutting instrument or handpiece as will be more apparent from the later description relative to FIG. 19. The transducer converts high frequency electrical energy to high frequency mechanical vibration to be transmitted to the surgical site. See e.g., International Application No. PCT/US87/00696, entitled "Method and Apparatus for Ultrasonic Surgical Fragmentation" published under WO87/05793. It further includes an elongated thin-wall vibration-transmitting tube shown generally at 34 which is separable from the horn 32 as best illustrated in FIG. 1. A retaining nut shown generally at 36 is provided to be threaded into position to hold the proximal end 38 of the tube 34 and the transition horn 32 together so that ultrasonic vibrations from the ultrasonic transducer can thereby be efficiently transmitted to the tube 34 and emitted from the distal end 40 of the tube 34 to the tissue at the surgical site.

Figure 2:
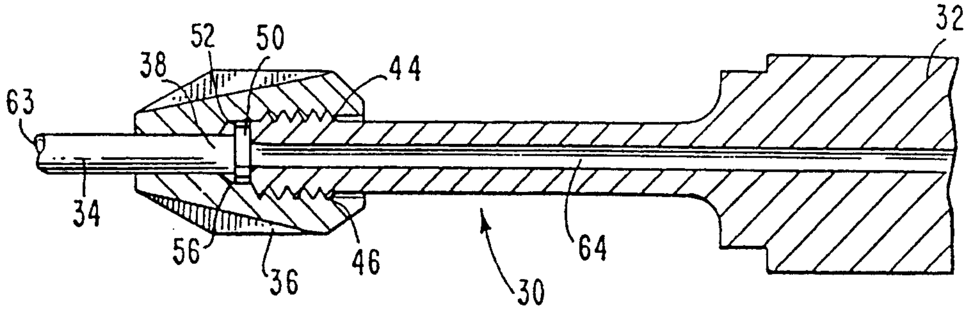
FIG. 2 is a longitudinal cross-sectional view of the embodiment of FIG. 1.

The horn 32 at its distal end has a threaded portion 44 on its outside surface. The retaining nut 36 at its proximal end similarly has internal threads 46, as best shown in FIG. 2, which are adapted to thread on to the horn threaded portion 44. The tube 34 at its proximal end has an annular flange 50 and three equally-spaced tabs 52 extending out therefrom. The retaining nut 36 preferably comprises a 3 AL-2.5 V or 6 AL-4 V titanium nut for strength, improved manufacturing dimensional accuracy, optimal finish, biocompatibility and low tooling cost, and it can be machined from a solid or tubular piece of titanium. The retaining nut 36 has an opening 54 extending longitudinally through it and the distal end 40 of the tube 34 passes out through it until the annular flange 50 engages an annular internal shoulder 56 as best shown in FIG. 2. The shoulder 56 is configured to be slightly smaller than the outer diameter of the tabs 52 so that an interference fit is thereby defined to more firmly hold the tube 34 to the nut 36 and eliminate seperation during attachment to the transition horn 32.

Figure 3:
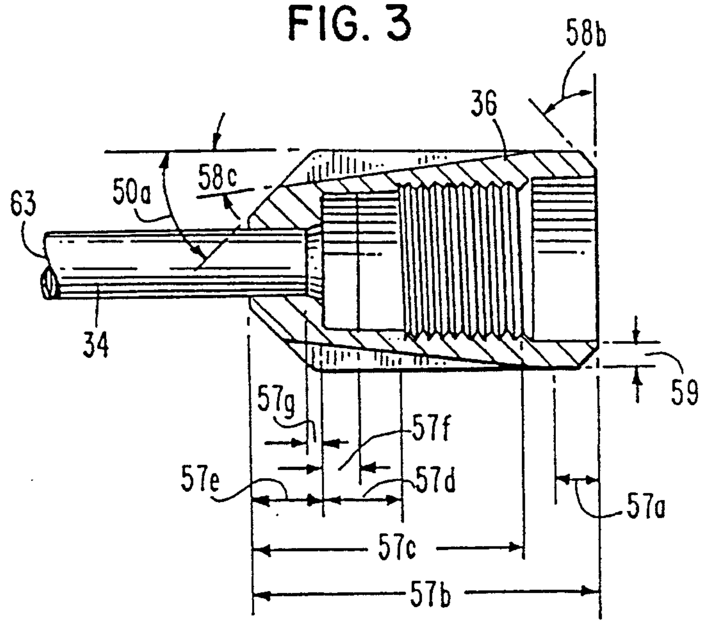
FIG. 3 is a longitudinal sectional view of the retaining nut and tube of the embodiment of FIG. 1.
Figure 4:
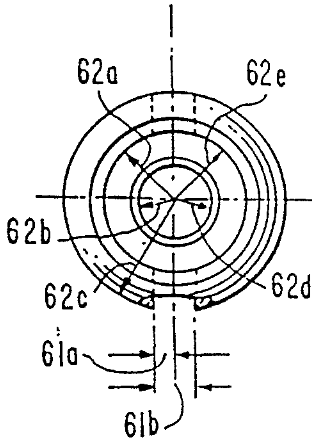
FIG. 4 is an end view of the retaining nut and tube of FIG. 3.

As can be appreciated, the design of assembly 30 allows for a minimum contact of the walls of the tube 34 to the retaining nut 36 thereby minimizing any ferriting corrosion, and allowing for a long extending tube length to be used. Referring to FIG. 3, the nut 36 has lengths in inches of 0.30, 0.240, 0.140, 0.055, 0.050, 0.025, and 0.010, as shown respectively at *57a*, *57b*, *57c*, *57d*, *57e*, *57f* and *57g*, angles of forty-five degrees as shown at *58a* and *58b*, an angle of 6°27'30" at *58c*, a width of 0.015 at 59, widths of 0.015 and 0.030 at *61a* and *61b* in FIG. 4 and diameters of 0.095, 0.054, 0.150, 0.002 and 0.115, as shown at *62a*, *62b*, *62c*, *62d* and *62e*.

The distal tip 40 of the tube 34 is configured to effectively transmit the ultrasonic energy to the surgical site and preferably has a flat ninety degree configuration as illustrated, but alternatively may have a curved or a cut angled or any other suitable configuration. See e.g. U.S. Pat. No. 3,589,363 (previously incorporated by reference) and U.S. Pat. No. 3,990,452. For example, U.S. Pat. No. 3,589,363 discloses a distal tip configuration having a concave shaped inside diameter. This concave shape produces a cone shaft wherein the inside diameter of the body of the shaft is larger than the inside diameter of the distal end or tip of the shaft. The distal tip 40 itself defines a thin wall, very sharp cutting edge. The tube 34 is preferably formed of stainless steel to minimize its unit cost and weight, to optimize the finish thereof and to provide greater strength and design flexibility. The tube 34 is hollow thereby defining a longitudinal channel 63 so that fluid and matter sucked through the distal tip 40 thereof can be aspirated through the entire length of the tube and then through the longitudinal channel 64 of the horn 32 and to a suitable container (not shown) as will become more apparent from the discussion to follow relative to FIG. 19.

Figure 5:
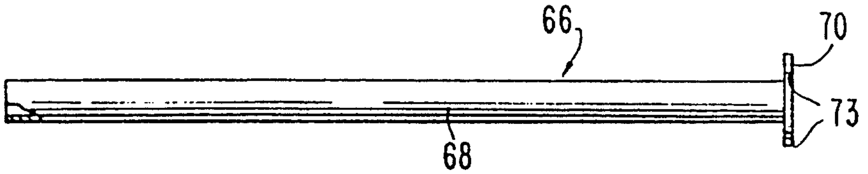
FIG. 5 is an elevational view of a first tube design of the present invention.
Figure 6:
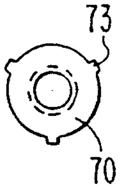
FIG. 6 is an end view of the tube of FIG. 5.

FIG. 5 is an elevational view and FIG. 6 is an end view of a tube which can be used with the assembly 30 of FIG. 1 and with a small end portion thereof broken away to illustrate its hollow configuration. The tube 66 is seen to simply comprise a cylinder 68 having a wall thickness of 0.0025 inch and an outer diameter of 0.042 inch. The flange 70 thereof has a thickness of 0.004 inch and the tube 66 has a length of 1.15 inch. The flange 70 has an outer diameter of 0.092 inch and each of the three radial tabs 72 thereon has a radial length of 0.003 inch and a width of 0.105 inch. It is noted in this regard that prior art tubes typically have a length shorter than 0.75 inches and a wall thickness greater than 0.004 inch. The flange 70 can range from about 5 degrees to 90 degrees.

Figure 7:
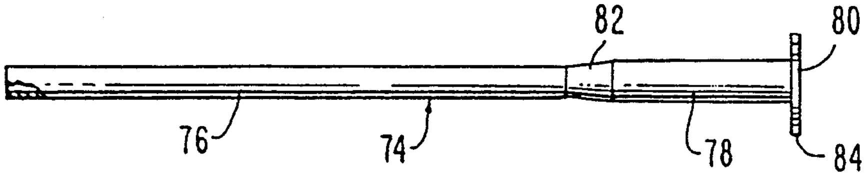
FIG. 7 is an elevational view of a second tube design of the present invention.
Figure 8:
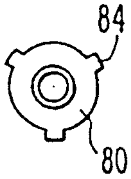
FIG. 8 is an end view of the tube of FIG. 7.

A second embodiment of a tube, which can be used with the assembly 30 and is also preferably formed of stainless steel, is illustrated in FIGS. 7 and 8 generally at 74. Tube 74 can be used for smaller incision procedures, and it is seen to comprise a cylindrical distal portion 76 having a distal portion outer diameter and a cylindrical proximal portion 78 adjoining the end flange 80 and having a proximal portion outer diameter. The proximal portion outer diameter is greater than the distal portion outer diameter and a conical portion 82 between and connecting the proximal and distal portions and tapering with an angle of seven degrees ± three degrees is provided having its outer diameter tapering from the proximal portion 78 to the distal portion 76. Tabs 84 can be provided on the end flange 80. In a preferred construction the distal portion outer diameter is 0.030 inch, the distal portion wall thickness is 0.0025 inch, the proximal portion outer diameter is 0.042 inch, the tube has a length of 1.150 inch and the distal portion has a length of 0.900 inch. The flanges of either one of these tube embodiments can be formed by swaging.

Figure 9:
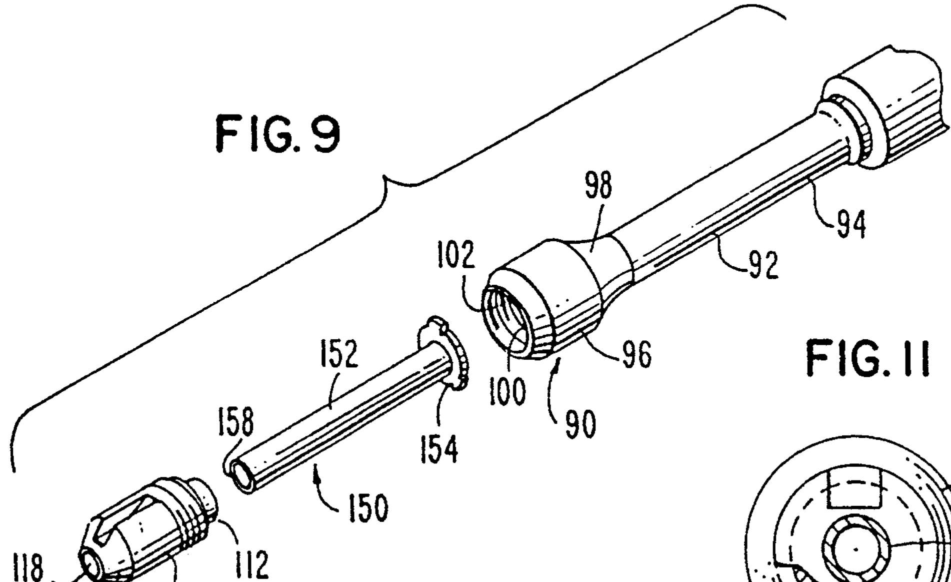
FIG. 9 is an exploded perspective view of a second embodiment of the present invention.
Figure 11:
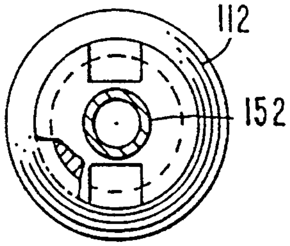
FIG. 11 is a cross-sectional view taken along line 11—11 of FIG. 10.
Figure 10:
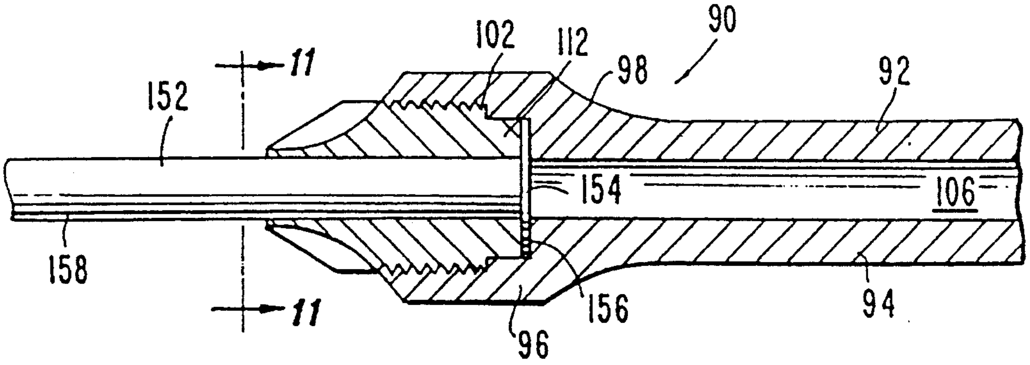
FIG. 10 is a longitudinal cross-sectional view of the embodiment of FIG. 9.

A second and preferred ultrasonic cutting tool assembly is illustrated in FIGS. 9 through 11 generally at 90 and either one of the tube designs of FIGS. 5 or 7 can be used therefor but preferably the tabs 72, 86 thereof are to be omitted. The cutting tool assembly 90 includes a transition horn 92 having a cylindrical portion 94 with a bulbous enlarged member 96 at its distal end. The curved connection surface 98 therebetween has a tangent which is less than or equal to twenty-two and half degrees. The enlarged member 96 has a large opening 100 extending about three-quarters of the way thereinto, as best seen in FIG. 10, and has internal threads 102 along its surface. The threads 102 extend to generally the end 104 of the enlarged opening and the opening 100 communicates with a narrower aspiration conduit 106 passing through the rest of the enlarged member 96, and through the cylindrical portion 94. The retaining nut 108 of this assembly is configured to be generally cylindrical in shape with a tapered front end 110 and a short stub portion 112 at its proximal end. A rear portion of the retaining nut 108 has external 4-80 threads 116 on its outside surface which are adapted to thread into the internal threads 102 of the horn 92. As depicted a conduit 118 passes longitudinally through the retaining nut 108.

Figure 12:
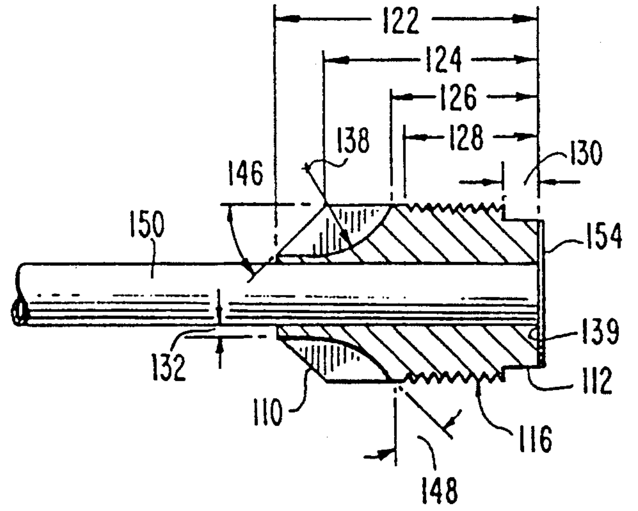
FIG. 12 is a cross-sectional view of the retaining nut and tube of the embodiment of FIG. 9 shown assembled together.
Figure 13:
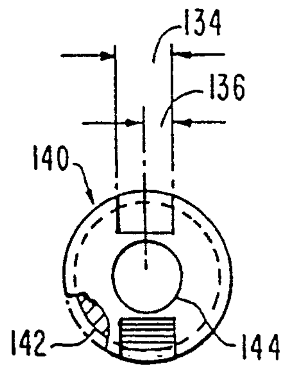
FIG. 13 is an end view of the assembled retaining nut and tube of FIG. 12.

Oppositely disposed forward notches 120 are formed in the front surface of the retaining nut 106, and the notches 120 are adapted to being engaged by a wrench, as will be discussed later, for manually rotating the nut 108 into threading engagement with the enlarged member 96. Referring to FIGS. 12 and 13, the retaining nut 108 has preferred dimensions in inches of 0.175, 0.140, 0.100, 0.090, 0.025, 0.005, 0.040, 0.020 as shown in FIG. 12 respectively at 122, 124, 126, 128, 130, 132, 134, and 136, a radius 138 of 0.062 inch, a minimum radius 139 of 0.008 inch, diameters in inches of 0.113, 0.092 and 0.045, as shown respectively at 140, 142 and 144, and two forty-five degree angles as shown at 146 and 148 and 4-80 threads at 149. The design of the assembly 90 provides excellent contact with the outer diameter of the tube 150, and is relatively easy and inexpensive to manufacture.

The tube 150 of this assembly, as was previously described with respect to FIGS. 5–8, has a cylindrical portion 152 adapted to pass into and through the conduit 118 of the retaining nut 108, and a flange 154 at its proximal end. Then when the cylindrical portion 152 of of the tube is passed out through the conduit 118 of the retaining nut 108 and the retaining nut 108 screwed into the enlarged member 96, the flange 154 is forced against of the internal shoulder 156 of the enlarged member 96 and held securely therein and positioned so that the conduit 158 of the tube 150 is aligned with the conduit 159 in the horn 92.

Figure 16:
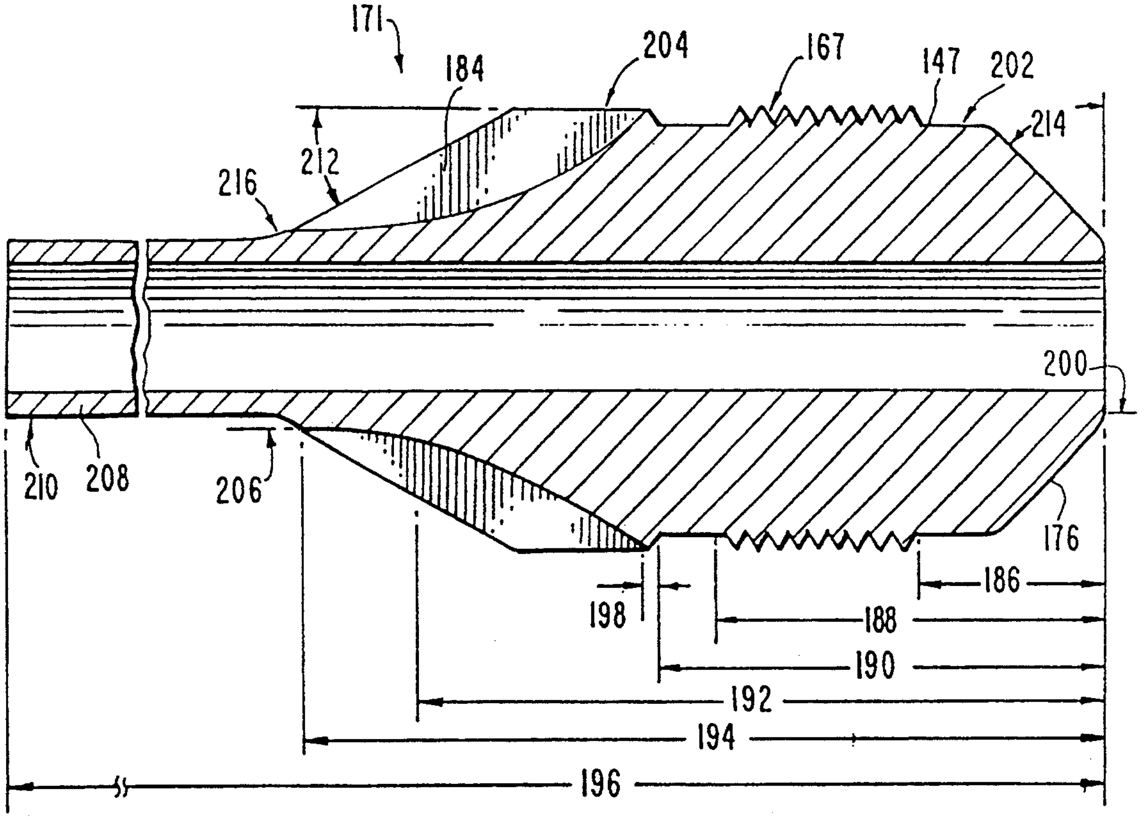
FIG. 16 is an enlarged cross-sectional view of the integral nut-tube member of the assembly of FIG. 14 illustrated in isolation.
Figure 14:
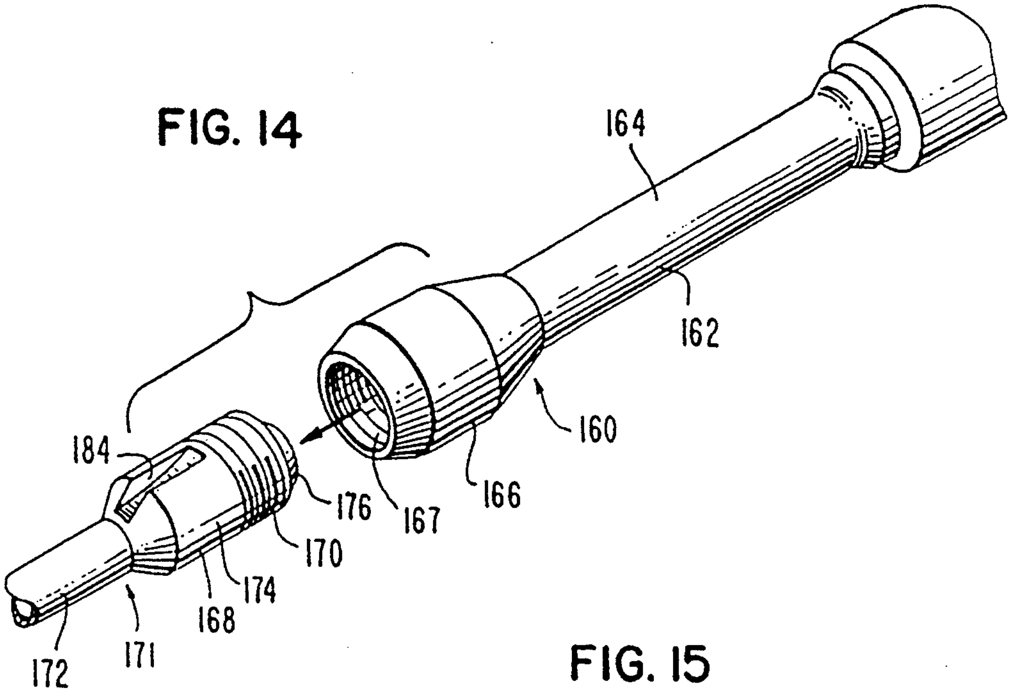
FIG. 14 is an exploded perspective view of a third embodiment of the present invention.
Figure 15:
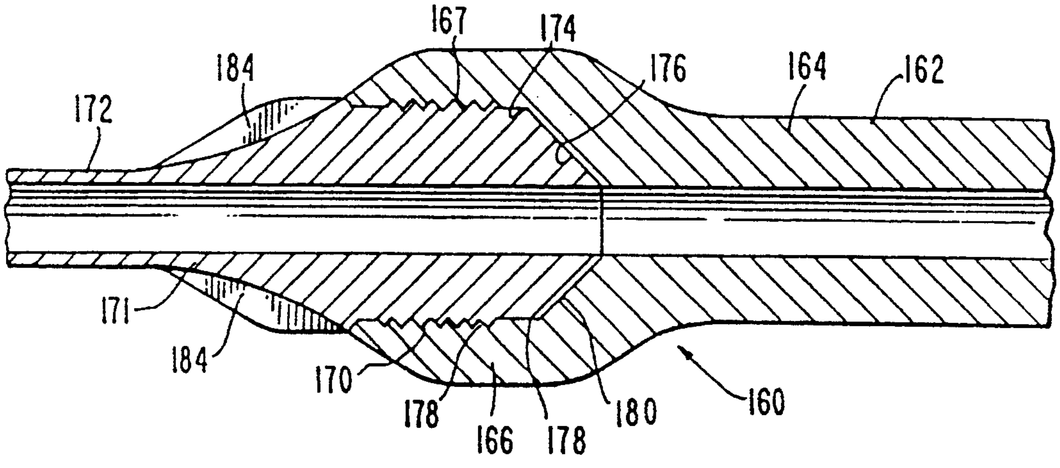
FIG. 15 is a longitudinal cross-sectional view of the embodiment of FIG. 14.

A third embodiment of the ultrasonic cutting tip assembly of the present invention is illustrated generally at 160 in FIGS. 14–16. It is seen therefrom that this embodiment is very similar to cutting tool assembly 90 in that it also has a horn 162 with a central cylindrical portion 164 and a bulbous enlarged member 166 having internal threads 167 therein. The retaining nut 168 with the external threads 170 thereon is formed, however, as a single piece shown generally at 171 with the tube 172 in this embodiment, and is preferably made from extruded 3 AL-2.5 V titanium. At its proximal end the nut 168 has a short cylindrical portion 174 generally of the same diameter as the immediately adjacent threaded portion 170 and a cone-shaped portion 176 extends rearwardly therefrom. As best shown in FIG. 13, the cylindrical and cone-shaped portions 174, 176 of the retaining nut 168 fit tightly against the similarly configured internal cylindrical and cone-shaped portions 178, 180, respectively, in the opening in the enlarged member 166. When the nut 168 is threaded tightly into and against the enlarged member 166 the ultrasonic vibrations are efficiently transferred to the tube 172 via the integral retaining nut 168.

The retaining nut 168 of this embodiment also has a pair of a wrench notches 184 on its forward surface. These elongated notches 184 provide engagement surfaces for a tightening wrench which can be slid into position in the notches and when turned so as to twist the retaining nut 168 about the longitudinal axis of the horn 162 will engage the sides of the notches. Referring to FIG. 16, the integral tube/nut member 171 has preferred dimensions in inches of 0.040, 0.095, 0.110, 0.175, 0.205, 1.055, 0.015, as shown respectively at 186, 188, 190, 192, 194, 196 and 198, distances to the longitudinal centerline of 0.044, 0.085, 0.115, 0.054, 0.036 (the inner radius of the tube) and 0.044 (the outer radius of the tube) as shown respectively at 200, 202, 204, 206, 208 and 210, an angle 212 of forty-five degrees or less and preferably thirty degrees, an angle 214 which is between forty-five and ninety degrees and preferably forty-five degrees, and a 0.030 minimum inch radius at 216. The notches or slots 184 are each 0.036 inch wide and positioned one hundred and eighty degrees relative to each other.

Figure 17:
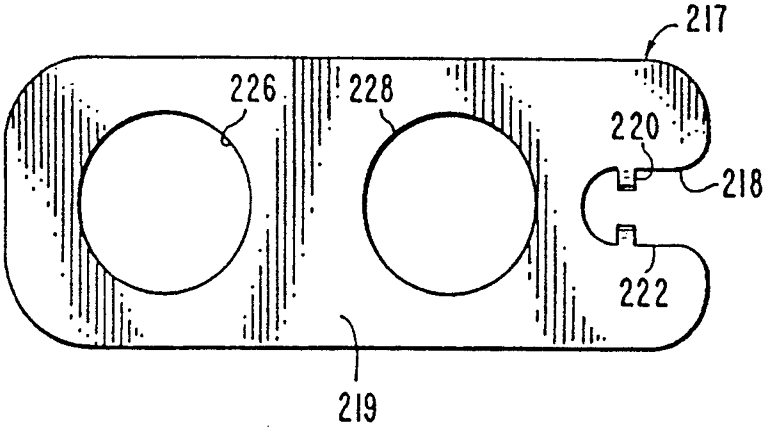
FIG. 17 is a plan view of a wrench for tightening the retaining nut relative to the horn of any of the embodiments herein.
Figure 18:
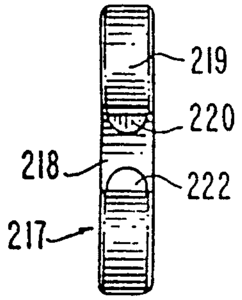
FIG. 18 is a right end view of the wrench of FIG. 17.

A suitable wrench is illustrated generally at 2 17 in FIGS. 17 and 18, is designed in a beer can tab of arrangement and can be adapted to be either disposable or reusable. It fits the tip nut 168 (or 36 or 108) from either the front or back of the wrench. The wrench 217 is formed by an elongated flat body member 219 of a suitable material, such as a metal or strong plastic, and has at its forward end a slot 218 extending longitudinally a distance towards the center thereof. The slot 218 has a pair of opposed rounded or semi-circular bibs 220, 222 extending laterally into the channel defined by the slot 218. These bibs 220, 222 are configured to slide into and engage in the notches 184 and then when the body member 219 is grasped and rotated, the retaining nut 168 can be turned and screwed relative to the horn 162.

Moles 226, 228 therethrough are formed to make the wrench 217 lighter and to allow it to cool down more quickly after having been auto-claved. The front and back edges of the bibs are sharp and all other wrench edges are well rounded. The wrench 217 has a width of 0.38 inch, a length of 0.75 inch and a thickness of 0.040 to 0.062 inch. The slot 218 has a rearward dimension from the middle of the bib of 0.075 inch and a forward dimension from the middle of the bib forward of 0.15 inch. As best shown in FIG. 15, each of the bibs has a radius of 0.125 inch and a distance between the innermost points of the bibs of 0.054 inch.

Figure 19:
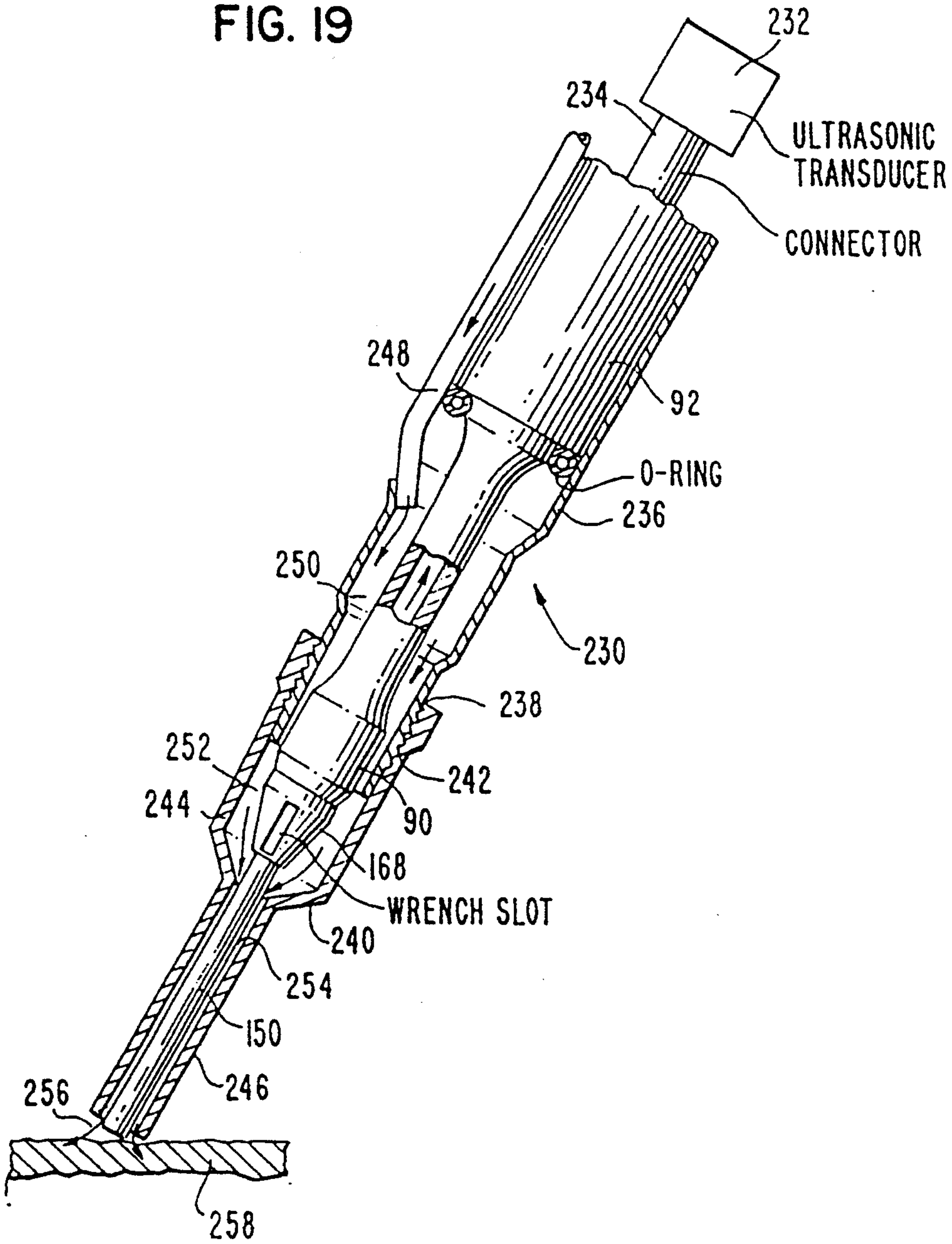
FIG. 19 is a fragmentary side view of a sample ultrasonic surgical cutting instrument using the ultrasonic cutting tip assembly of FIGS. 9–13.

In FIG. 19 the assembly 90 of FIGS. 9 through 11 is illustrated in position in an ultrasonic cutting tool instrument or handpiece shown generally at 230. Since many handpiece constructions are known, such as the "Model 500 Ultrasonic Surgical Handpiece" of The Cooper Companies, Inc., or the site TXR Ultrasonic handpiece, or the Optikon Ultrasonic handpiece and this cutting tip assembly 90 (or 30 or 160) can be adapted for practically any of them, only the forward portion of the handpiece 230 surrounding the cutting tip assembly 90 is illustrated. The ultrasonic transducer 232 and the connector 234 thereof are shown schematically. The connector 234 provides an operative connection between the transducer 232 and the transition horn (a stepped sectional concentrator) 92, and, for example, can simply comprise a rigid mounting of the horn 92 to the transducer 232.

The handpiece 230 includes an outer shell body 236 encircling the cutting tip assembly 90 and having threads 238 at its end. A tip-cap-sleeve 240 having internal threads 242 threads onto the shell body 236 and has an outer cylindrical portion 244 surrounding the retaining nut 108 and tapering to a narrower elongated cylindrical portion 246 surrounding the tube 150. An irrigation tube 248 communicating with a suitable irrigation fluid supply (not shown) passes along the outside of the shell body 236 and then passes in through an opening in the shell body 256 adjacent the transition horn 92. The irrigation fluid flows from the tube 248 into the passage 250 defined between the outer shell body 236 and the horn 92, to the passage 252 defined between the retaining nut 108 and the tip cap sleeve, into the annular space 254 between the forward portion of the sleeve and the tube 150 and then out the end 256 to the surgical site 258. Different manifold and fitting designs are disclosed in International application number PCT/US87/00795 entitled "Irrigation/Aspiration Manifold and Fittings for Ultrasonic Surgical Aspiration System" and published under No. WO87/06116. An ultrasonic decoupling sleeve (not shown) as taught in U.S. Pat. No. 4,681,561 to Hood et al can also be provided.

An aspiration pressure source (not shown) communicates with the aspiration conduit 106 of the transition horn 92 so as to create a suction pressure in this channel whereby material at the surgical site 258 ultrasonically dislodged and cut or emulsified by the ultrasonic energy of the tip of the tube 150 and suspended in the irrigation or body fluids is withdrawn through the interior of the tube 150, the retaining nut 108, and the transition horn 92 and thereby away from the surgical site 258 to a suitable collection container (not shown). Systems for controlling the flow of irrigation and aspiration fluid are discussed in International Application No. PCT/US86/01186, published under No. WO86/07249, and also in U.S. Pat. No. 3,693,613.

By the unique design of each of these cutting tip assembly embodiments so to eliminate all exposed tip nut surface angles greater than forty-five degrees, a substantial improvement in hydrodynamic performance is achieved. The larger the surface areas at ninety degrees to the ultrasonic tool motion, the greater the loading of the tool, the more power required to obtain the tool tip end stroke, and the more cavitation-generated bubbles which can visually obscure the surgical procedure especially cataract removal procedures. Also, the present cutting tip assembly designs which allow the length of the tube to be increased and the wall thickness decreased result in an increase of more than fifty percent in the amplitude the stroke of the tube tip. The peak stroke of the tip is at least 0.008 inch and preferably 0.004 inch, and the tip is vibrating at a frequency of between 20 and 250 kHz and preferably 60 kHz. It is anticipated that in a cataract lens removal procedure this combined tip-nut load reduction and tip tube stroke gain will reduce the ultrasonic handpiece power requirements and the consequent undesirable heating of and ultrasound exposure to the eye by more than fifty percent without any accompanying reduction in the cataract lens removal performance. Also reduction of the ultrasonic energy used during the surgical procedure will reduce the adjacent tissue heating experienced with prior art handpieces. This heating is known to cause corneal burns, astigmatism and other problems. Further, by reducing the cavitation erosion previously experienced, resulting metallic particulate deposition in the eye is thereby reduced.

An improved coupling between the ultrasonic transition horn and the tip of the ultrasonic tool is provided by the embodiments of this invention. By changing from 4-40 threads to 4-80 threads a higher compressional force for the torque is allowed. This higher force together with the reduced cross-sectional area of the tube and horn interface, i.e. from an outer diameter of 0.138 inch to an outer diameter of 0.092 inch, provide an improved, lower impedance ultrasonic energy coupling of the tube tip and the horn, and a better fluid seal therebetween. The 4-80 thread design reduces the cross-sectional area changes in the ultrasonic horn and thereby reduces acoustic gain variations and increases the stability of the handpiece. This tube tip and retaining nut design should accommodate tensile pressures greater than 30,000 psi and accelerations of 300,000G minimum.

The tube designs herein having a thin tube wall thickness, and a constant, non-tapered, non-stepped inner and outer diameters allow a more linear tip gain or stroke increase, a more even tip stress distribution and a lower thermal resistance. The reduced cross-sectional area of the tube cutting edge together with increased sharpness thereof significantly increase the pressure thereby exerted to break the bonds holding the cataract lens or other material together. The high acceleration in the order of 300,000G and the minimal cross-sectional area of the tip cutting edge provided by its thin wall and ultra-sharp construction produce a very high inertial fixation, which means that tissue resection can be performed on harder cataract lenses with less disturbance to surrounding tissue.

Although the ultrasonic cutting tip assemblies described herein are firstly used for ophthalmic cataract surgery lens removal, they can also adapted and used with a low pain hypodermic syringe injectors having non-coring, super-lubricated, disposable tips, with general surgical high-speed tissue resection instruments, or with similar instruments. Also, some of the improvements of the present tube-nut design can be used in known one-piece titanium tip-nut constructions.

The length, angles and other dimensions are for illustration purposes unless indicated as being important or critical.

From the foregoing detailed description, it will be evident that there are a number of changes, adaptations, and modifications of the present invention which come within the province of those skilled in the art. However, it is intended that all such variations not departing from the spirit of this invention be considered as within the scope thereof as limited solely by the claims appended hereto.

What is claimed is:

1. For an ultrasonic surgical cutting instrument having an ultrasonic transducer, an ultrasonic cutting tip assembly comprising:

a transition horn operatively couplable to the ultrasonic transducer, a vibration-transmitting tube separable from said horn and having a tube proximal end and a tube distal end, a line between the tube distal end and the tube proximal end defining a longitudinal direction; and a retaining nut adapted to engage said transition horn to hold said tube proximal end and said transition horn together so that ultrasonic vibrations can thereby be transmitted to said tube and emitted from said tube distal end to the surgical site, wherein:

said retaining nut and said tube are formed as a single piece with said tube extending out from said retaining nut, and said retaining nut has at least one nut wrench notch extending in the longitudinal direction from a forward end of said nut and adapted to be engaged by a wrench for turning said retaining nut to secure said retaining nut to said transition horn.

2. The assembly of claim 1 wherein said transition horn has a horn distal end and defines a horn end opening at said horn distal end, said transition horn has a threaded portion disposed inside of said horn end opening, and said retaining nut has a threaded portion disposed on an outside surface of said retaining nut.

3. The assembly of claim 2 wherein said tube proximal end is disposed inside of said horn end opening.

4. The assembly of claim 3 wherein said horn end opening has an internal shoulder at a proximal end thereof against which said tube is held by said retaining nut.

5. The assembly of claim 4 wherein said tube has an annular flange at its proximal end which abuts against said internal shoulder when said tube and said transition horn are held together by said retaining nut.

6. The assembly of claim 1 wherein said transition horn includes a threaded portion which comprises external threads thereon and said retaining nut includes a threaded portion which comprises internal threads therein such that said retaining nut threads onto said horn.

7. The assembly of claim 1, wherein all exposed surfaces of said retaining nut have angles no greater than forty five degrees with respect to lines parallel to said line between the tube distal end and the tube proximal end.

8. The assembly of claim 1 wherein said tube has a length of 0.850 inch and at its distal tube end a wall thickness of 0.0025 inch.

9. The assembly of claim 1, wherein said transition horn comprises a threaded portion and said retaining nut comprises a threaded portion each of which have 4-80 threads.

10. The assembly of claim 1 wherein said retaining nut is formed of titanium.

11. The assembly of claim 10 wherein said titanium is 3 Al-2.5 V titanium.

12. The assembly of claim 1 wherein said retaining nut and said tube define a cylindrical passageway of uniform diameter extending therethrough.

13. The assembly of claim 1 wherein said retaining nut has a nut outer surface and a threaded portion disposed on said nut outer surface.

14. The assembly of claim 1 wherein the ultrasonic surgical cutting instrument includes a sleeve surrounding said retaining nut and extending forwardly past said retaining nut and around said tube.

15. The assembly of claim 1 wherein said retaining nut has a forward surface at an angle not greater than forty-five degrees with respect to a line parallel to said line between the tube distal end and the tube proximal end.

16. The assembly of claim 15 wherein said angle is thirty degrees.

17. The assembly of claim 15 wherein said retaining nut includes a nut threaded portion which defines external threads and said retaining nut has a rearward surface at an angle generally between forty-five degrees and ninety digress with respect to a line parallel to said line between the tube distal end and the tube proximal end.

18. The assembly of claim 17 wherein the angle of said rearward surface is forty-five degrees.

19. The assembly of claim 17 wherein said retaining nut has a generally cylindrical portion between and adjacent the forward and rearward surfaces thereof and said nut threaded portion is on said cylindrical portion.

20. The assembly of claim 15 wherein said transition horn has a forward cylindrical portion and an enlarged portion at the distal tip of said cylindrical portion and said transition horn has a threaded portion disposed of inside of said enlarged portion.

21. The assembly of claim 20 wherein said enlarged portion has a rearward surface at an angle not greater than twenty-two and a half digress with respect to a line parallel to said line between the tube distal end and the tube proximal end.

22. The assembly of claim 15 wherein said retaining nut includes a nut threaded portion which defines surface at an angle not greater than forty-five digress with respect to a line parallel to said line between the tube distal end and the tube proximal end.

23. The assembly of claim 22 wherein the angle of said rearward surface is thirty degrees.

24. The assembly of claim 23 wherein the angle of said forward surface is thirty degrees.

25. The assembly of claim 22 wherein said transition horn has a forward cylindrical portion and a threaded portion positioned on the distal end of said forward cylindrical portion.

26. The assembly of claim 1 wherein said tube distal end has a wall thickness of about 0.0025 inch and an outer diameter of about 0.042 inch.

27. The assembly of claim 1 wherein said tube defines an aspiration passageway therethrough for aspirating fragmented tissue and fluid away from the surgical site.

28. The assembly of claim 1 wherein said tube distal end defines a tip which is flat and perpendicular to said tube.

29. The assembly of claim 1 wherein said tube and said retaining nut are adapted to accommodate a force greater than 30,000 psi and an acceleration of at least 300,000G.

30. The assembly of claim 1 wherein said tube includes a radial flange at the proximal tube end and a cylinder extending from said flange to the distal tube end.

31. For an ultrasonic surgical cutting instrument having an ultrasonic transducer, an ultrasonic cutting tip assembly comprising:

a transition horn operatively couplable to the ultrasonic transducer;

a vibration-transmitting tube separable from said horn and having a tube proximal end and a tube distal end, said tube comprising a cylindrical distal portion having a distal portion outer diameter, a cylindrical proximal portion having a proximal portion outer diameter, said proximal portion outer diameter being greater than said distal portion outer diameter, and a conical portion between and connecting said proximal and distal portions, said conical portion having its outer diameter tapering from said proximal portion to said distal portion; and a retaining nut adapted to engage said transition horn to hold said tube proximal end and said transition horn together so that ultrasonic vibrations can thereby be transmitted to said tube and emitted from said tube distal end to the surgical site, wherein said retaining nut and said tube are formed as a single piece with said tube extending out from said retaining nut.

32. The assembly of claim 31 wherein said distal portion outer diameter is about 0.030 inch and said proximal portion outer diameter is about 0.042 inch.

33. The assembly of claim 32 wherein said tube has a length of about 1.15 inch and said distal portion has a length of about 0.900 inch.

34. For an ultrasonic surgical cutting instrument having an ultrasonic transducer, an ultrasonic cutting tip assembly comprising:

a transition horn operatively couplable to the ultrasonic transducer, a vibration-transmitting tube separable from said horn and having a tube proximal end and a tube distal end; and a retaining nut adapted to engage said transition horn to hold said tube proximal end and said transition horn together so that ultrasonic vibrations can thereby be transmitted to said tube and emitted from said tube distal end to the surgical site, wherein:

said retaining nut and said tube are formed as a single piece with said tube extending out from said retaining nut; and said retaining nut has a pair of spaced wrench-engageable notches on the outer surface thereof.

* * * * *